(12) United States Patent
Mitani et al.

(10) Patent No.: US 7,354,754 B2
(45) Date of Patent: Apr. 8, 2008

(54) MICROORGANISM SENSITIVE TO LYSOZYME

(75) Inventors: Yasuo Mitani, Sapporo (JP); Nobutaka Nakashima, Sapporo (JP); Tomohiro Tamura, Sapporo (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 296 days.

(21) Appl. No.: 10/524,630

(22) PCT Filed: Aug. 14, 2003

(86) PCT No.: PCT/JP03/10342

§ 371 (c)(1),
(2), (4) Date: Feb. 16, 2005

(87) PCT Pub. No.: WO2004/018651

PCT Pub. Date: Mar. 4, 2004

(65) Prior Publication Data

US 2006/0166312 A1 Jul. 27, 2006

(30) Foreign Application Priority Data

Aug. 20, 2002 (JP) ............................. 2002-239554

(51) Int. Cl.
*C12N 1/22* (2006.01)
(52) U.S. Cl. ..................................... 435/252
(58) Field of Classification Search ..................... None
See application file for complete search history.

(56) References Cited

FOREIGN PATENT DOCUMENTS

| | | |
|---|---|---|
| EP | 0 064 680 A2 | 11/1982 |
| JP | 61-280273 | 12/1986 |
| JP | 07-255484 | 10/1995 |

OTHER PUBLICATIONS

Hashimoto et al., Site-directed mutagenesis for cysteine residues of cobalt-containing nitrile hydratase, J Inorg Biochem. Jul. 2002 vol. 91, No. 1 pp. 70-77.*

Arensdorf et al., Chemostat approach for the directed evolution of biodesulfurization gain-of-function mutants, Environ Microbiol. Feb. 2002, vol. 68, No. 2, pp. 691-698.*

Bailey et al,. "Emulsification of Crude Oil by *Rhodococcus erythropolis* Strain ST-2 via a Cell-Surface, Lysozyme-Sensitive Glycoprotein," System. Appl. Microbiol., 1997, vol. 20, pp. 545-548.

Inoue et al., "Isolation and Characterization of Lysozyme-Sensitive Mutants of *Staphylococcus aureus*," Journal of Bacteriology, Dec. 1980, pp. 1186-1189.

Hirasawa et al., "A Mutation in the *Corynebacterium glutamicum ItsA* Gene Causes Susceptibility to Lysozyme, Temperature-Sensitive Growth, and L-Glutamate Production," Journal of Bacteriology, May 2000, pp. 2696-2701.

* cited by examiner

*Primary Examiner*—Robert B. Mondesi
(74) *Attorney, Agent, or Firm*—Foley & Lardner LLP

(57) ABSTRACT

A microorganism of the genus *Rhodococcus* is provided which has a higher sensitivity to lysozyme at a low concentration than a wild-type strain, which can easily cause cell lysis, and from which a recombinant protein expressed therein is easily recovered. More specifically, a mutant microorganism of the genus *Rhodococcus* having a higher sensitivity to lysozyme than a wild-type microorganism of the genus *Rhodococcus*.

1 Claim, 5 Drawing Sheets (2 of 5 Drawing Sheet(s) Filed in Color)

SEQUENCE LISTING

```
<160> NUMBER OF SEQ ID NOS: 2

<210> SEQ ID NO 1
<211> LENGTH: 5108
<212> TYPE: DNA
<213> ORGANISM: Artificial Sequence
<220> FEATURE:
<223> OTHER INFORMATION: Description of Artificial Sequence: Plasmid
      pHN144

<400> SEQUENCE: 1
gagctcgacc gcgcgggtcc cggacgggga agagcgggga gctttgccag agagcgacga          60
cttccccttg cgttggtgat tgccggtcag ggcagccatc cgccatcgtc gcgtagggtg         120
tcacacccca ggaatcgcgt cactgaacac agcagccggt aggacgacca tgactgagtt         180
ggacaccatc gcaaatccgt ccgatcccgc ggtgcagcgg atcatcgatg tcaccaagcc         240
gtcacgatcc aacataaaga caacgttgat cgaggacgtc gagcccctca tgcacagcat         300
cgcggccggg gtggagttca tcgaggtcta cggcagcgac agcagtcctt ttccatctga         360
gttgctggat ctgtgcgggc ggcagaacat accggtccgc ctcatcgact cctcgatcgt         420
caaccagttg ttcaagggggg agcggaaggc caagacattc ggcatcgccc gcgtccctcg         480
```

-continued

```
cccggccagg ttcggcgata tcgcgagccg gcgtggggac gtcgtcgttc tcgacggggt    540
gaagatcgtc gggaacatcg gcgcgatagt acgcacgtcg ctcgcgctcg gagcgtcggg    600
gatcatcctg gtggacagtg acatcaccag catcgcggac cggcgtctcc aaagggccag    660
ccgaggttac gtcttctccc ttcccgtcgt tctctccggt cgcgaggagg ccatcgcctt    720
cattcgggac agcggtatgc agctgatgac gctcaaggcg gatggcgaca tttccgtgaa    780
ggaactcggg gacaatccgg atcggctggc cttgctgttc ggcagcgaaa agggtgggcc    840
ttccgacctg ttcgaggagg cgtcttccgc ctcggtttcc atccccatga tgagccagac    900
cgagtctctc aacgtttccg tttccctcgg aatcgcgctg cacgagagga tcgacaggaa    960
tctcgcggcc aaccgataag cgcctctgtt cctcggacgc tcggttcctc gacctcgatt   1020
cgtcagtgat gatcacctca cacggcagcg atcaccactg acatatcgag gtcaacggtc   1080
gtggtccggg cggcactcc tcgaaggcgc ggccgacgcc cttgaacgac tcgatgactc    1140
tagaggatcc ccgggtaccg agctcgtcag gtggcacttt tcgggaaat gtgcgcggaa    1200 cccctatttg tttattttc taaatacatt caaatatgta tccgctcatg agacaataac    1260
cctgataaat gcttcaataa tattgaaaaa ggaagagtat gagtattcaa catttccgtg    1320
tcgcccttat tcccttttt gcggcatttt gccttcctgt ttttgctcac ccagaaacgc    1380
tggtgaaagt aaaagatgct gaagatcagt tgggtgcacg agtgggttac atcgaactgg    1440
atctcaacag cggtaagatc cttgagagtt ttcgccccga agaacgtttt ccaatgatga    1500
gcacttttaa agttctgcta tgtggcgcgg tattatcccg tattgacgcc gggcaagagc    1560
aactcggtcg ccgcatacac tattctcaga atgacttggt tgagtactca ccagtcacag    1620
aaaagcatct tacggatggc atgacagtaa gagaattatg cagtgctgcc ataaccatga    1680
gtgataacac tgcggccaac ttacttctga acgatcgg aggaccgaag gagctaaccg    1740
cttttttgca caacatgggg gatcatgtaa ctcgccttga tcgttgggaa ccggagctga    1800
atgaagccat accaaacgac gagcgtgaca ccacgatgcc tgtagcaatg gcaacaacgt    1860
tgcgcaaact attaactggc gaactactta ctctagcttc ccggcaacaa ttaatagact    1920
ggatggaggc ggataaagtt gcaggaccac ttctgcgctc ggcccttccg gctggctggt    1980
ttattgctga taaatctgga gccggtgagc gtgggtctcg cggtatcatt gcagcactgg    2040
ggccagatgg taagccctcc cgtatcgtag ttatctacac gacggggagt caggcaacta    2100
tggatgaacg aaatagacag atcgctgaga taggtgcctc actgattaag cattggtaac    2160
tgtcagacca agtttactca tatatacttt agattgattt aaaacttcat ttttaattta    2220
aaaggatcta ggtgaagatc ctttttgata atctcatgac caaaatccct aacgtgagt    2280 tttcgttcca ctgagcgtca gaccccgtag aaaagatcaa aggatcttct tgagatcctt    2340 ttttttctgcg cgtaatctgc tgcttgcaaa caaaaaaacc accgctacca gcggtggttt    2400
gtttgccgga tcaagagcta ccaactcttt ttccgaaggt aactggcttc agcagagcgc    2460
agataccaaa tactgttctt ctagtgtagc cgtagttagg ccaccacttc aagaactctg    2520
tagcaccgcc tacatacctc gctctgctaa tcctgttacc agtggctgct gccagtggcg    2580
ataagtcgtg tcttaccggg ttggactcaa gacgatagtt accggataag gcgcagcggt    2640
cgggctgaac ggggggttcg tgcacacagc ccagcttgga gcgaacgacc tacaccgaac    2700
tgagatacct acagcgtgag ctatgagaaa gcgccacgct tcccgaaggg agaaaggcgg    2760
acaggtatcc ggtaagcggc agggtcggaa caggagagcg cacagaggag cttccagggg    2820
gaaacgcctg gtatctttat agtcctgtcg ggtttcgcca cctctgactt gagcgtcgat    2880
```

```
ttttgtgatg ctcgtcaggg gggcggagcc tatggaaaaa cgccagcaac gcggcctttt    2940
tacggttcct ggccttttgc tggccttttg ctcacatgtt ctttcctgcg ttatcccctg    3000
attctgtgga taaccgtatt accgcctttg agtgagctga taccgctcgc cgcagccgaa    3060
cgaccgagcg cagcgagtca gtgagcgagg aagcggaaga gcgcccaata cgcaaaccgc    3120
ctctccccgc gcgttggccg attcattaat gcagctggca cgactagttg tacacccgag    3180
aagctcccag cgtcctcctg ggccgcgata ctcgaccacc acgcacgcac accgcactaa    3240
cgattcggcc ggcgctcgat tcggccggcg ctcgattcgg ccggcgctcg attcggccgg    3300
cgctcgattc ggccggcgct cgattcggcc gagcagaaga gtgaacaacc accgaccacg    3360
cttccgctct gcgcgccgta cccgacctac ctcccgcagc tcgaagcagc tcccgggagt    3420
accgccgtac tcacccgcct gtgctcacca tccaccgacg caaagcccaa cccgagcaca    3480
cctcttgcac caaggtgccg accgtggctt tccgctcgca gggttccaga agaaatcgaa    3540
cgatccagcg cggcaaggtt caaaaagcag gggttggtgg ggaggaggtt ttgggggtg    3600
tcgccgggat acctgatatg gctttgtttt gcgtagtcga ataattttcc atatagcctc    3660
ggcgcgtcgg actcgaatag ttgatgtggg cgggcacagt tgccccatga aatccgcaac    3720
gggggcgtg ctgagcgatc ggcaatgggc ggatgcggtg ttgcttccgc accggccgtt    3780
cgcgacgaac aacctccaac gaggtcagta ccggatgagc cgcgacgacg cattggcaat    3840
gcggtacgtc gagcattcac cgcacgcgtt gctcggatct atcgtcatcg actgcgatca    3900
cgttgacgcc gcgatgcgcg cattcgagca accatccgac catccggcgc cgaactgggt    3960
tgcacaatcg ccgtccggcc gcgcacacat cggatggtgg ctcggcccca accacgtgtg    4020
ccgcaccgac agcgcccgac tgacgccact gcgctacgcc caccgcatcg aaaccggcct    4080
caagatcagc gtcggcggcg atttcgcgta tggcgggcaa ctgaccaaaa acccgattca    4140
ccccgattgg gagcgatct acggcccggc caccccgtac acattgcggc agctggccac    4200
catccacaca ccccggcaga tgccgcgtcg gcccgatcgg gccgtgggcc tgggccgcaa    4260
cgtcaccatg ttcgacgcca cccggcgatg gcataccg cagtggtggc aacaccgaaa    4320
cggaaccggc cgcgactggg accatctcgt cctgcagcac tgccacgccg tcaacaccga    4380
gttcacgaca ccactgccgt tcaccgaagt acgcgccacc gcgcaatcca tctccaaatg    4440
gatctggcgc aatttcaccg aagaacagta ccgagcccga caagcgcatc tcggtcaaaa    4500
aggcggcaag gcaacgacac tcgccaaaca agaagccgtc cgaaacaatg caagaaagta    4560
cgacgaacat acgatgcgag aggcgattat ctgatgggcg gagccaaaaa tccggtgcgc    4620
cgaaagatga cggcagcagc agcagccgaa aaattcggtg cctccactcg cacaatccaa    4680
cgcttgtttg ctgagccgcg tgacgattac ctcggccgtg cgaaagctcg ccgtgacaaa    4740
gctgtcgagc tgcggaagca ggggttgaag taccggaaa tcgccgaagc gatgaaactc    4800
tcgaccggga tcgtcggccg attactgcac gacgcccgca ggcacggcga gatttcagcg    4860
gaggatctgt cggcgtaacc aagtcagcgg gttgtcgggt tccggccggc gctcggcact    4920
cggaccggcc ggcggatggt gttctgcctc tggcgcagcg tcagctaccg ccgaaggcct    4980
gtcatcgacc ggcttcgact gaagtatgag caacgtcaca gcctgtgatt ggatgatccg    5040
ctcacgctcg accgctacct gttcagctgc cgcccgctgg gcatgagcaa cggccaactc    5100
tcgttcaa                                                              5108
```

<210> SEQ ID NO 2

<211> LENGTH: 8971
<212> TYPE: DNA
<213> ORGANISM: Artificial Sequence
<220> FEATURE:
<223> OTHER INFORMATION: Description of Artificial Sequence: Plasmid pHN170

<400> SEQUENCE: 2

| | | | | | |
|---|---|---|---|---|---|
| gagctcgacc | gcgcgggtcc | cggacgggga | agagcgggga | gctttgccag | agagcgacga | 60 |
| cttccccttg | cgttggtgat | tgccggtcag | ggcagccatc | cgccatcgtc | gcgtagggtg | 120 |
| tcacacccca | ggaatcgcgt | cactgaacac | agcagccgga | aggacgacca | tgactgagtt | 180 |
| ggacaccatc | gcaaatccgt | ccgatcccgc | ggtgcagcgg | atcatcgatg | tcaccaagcc | 240 |
| gtcacgatcc | aacataaaga | caacgttgat | cgaggacgtc | gagcccctca | tgcacagcat | 300 |
| cgcggccggg | gtggagttca | tcgaggtcta | cggcagcgac | agcagtcctt | ttccatctga | 360 |
| gttgctggat | ctgtgcgggc | ggcagaacat | accggtccgc | ctcatcgact | cctcgatcgt | 420 |
| caaccagttg | ttcaagggggg | agcggaaggc | caagacattc | ggcatcgccc | gcgtccctcg | 480 |
| cccggccagg | ttcggcgata | tcgcgagccg | cgtgggggac | gtcgtcgttc | tcgacggggt | 540 |
| gaagatcgtc | gggaacatcg | gcgcgatagt | acgcacgtcg | ctcgcgctcg | gagcgtcggg | 600 |
| gatcatcctg | gtggacagtg | acatcaccag | catcgcggac | cggcgtctcc | aaagggccag | 660 |
| ccgaggttac | gtcttctccc | ttcccgtcgt | tctctccggt | cgcgaggagg | ccatcgcctt | 720 |
| cattcgggac | agcggtatgc | agctgatgac | gctcaaggcg | gatggcgaca | tttccgtgaa | 780 |
| ggaactcggg | gacaatccgg | atcggctggc | cttgctgttc | ggcagcgaaa | agggtgggcc | 840 |
| ttccgacctg | ttcgaggagg | cgtcttccgc | ctcggtttcc | atcccatga | tgagccagac | 900 |
| cgagtctctc | aacgtttccg | tttccctcgg | aatcgcgctg | cacagagga | tcgacaggaa | 960 |
| tctcgcggcc | aaccgataag | cgcctctgtt | cctcggacgc | tcggttcctc | gacctcgatt | 1020 |
| cgtcagtgat | gatcacctca | cacggcagcg | atcaccactg | acatatcgag | gtcaacggtc | 1080 |
| gtggtccggg | cggcactcc | tcgaaggcgc | ggccgacgcc | cttgaacgac | tcgatgactc | 1140 |
| tagagtaacg | ggctactccg | tttaacggac | cccgttctca | cgctttaggc | ttgaccccgg | 1200 |
| agcctgcatg | gggcattccg | ccgtgaaccc | ggtggaatgc | ccccggcacc | cgggctttcc | 1260 |
| agcaaagatc | acctggcgcc | gatgagtaag | gcgtacagaa | ccactccaca | ggaggaccgt | 1320 |
| cgagatgaaa | tctaacaatg | cgctcatcgt | catcctcggc | accgtcaccc | tggatgctgt | 1380 |
| aggcataggc | ttggttatgc | cggtactgcc | gggcctcttg | cgggatatcg | tccattccga | 1440 |
| cagcatcgcc | agtcactatg | gcgtgctgct | agcgctatat | gcgttgatgc | aatttctatg | 1500 |
| cgcacccgtt | ctcggagcac | tgtccgaccg | ctttggccgc | cgcccagtcc | tgctcgcttc | 1560 |
| gctacttgga | gccactatcg | actacgcgat | catggcgacc | acaccgtcc | tgtggattct | 1620 |
| ctacgccgga | cgcatcgtgg | ccggcatcac | cggcgccaca | ggtgcggttg | ctggcgccta | 1680 |
| tatcgccgac | atcaccgatg | gggaagatcg | ggctcgccac | ttcgggctca | tgagcgcttg | 1740 |
| tttcggcgtg | ggtatggtgg | caggccccgt | ggccggggga | ctgttgggcg | ccatctcctt | 1800 |
| gcatgcacca | ttccttgcgg | cggcggtgct | caacggcctc | aacctactac | tgggctgctt | 1860 |
| cctaatgcag | gagtcgcata | agggagagcg | tcgtccgatg | cccttgagag | ccttcaaccc | 1920 |
| agtcagctcc | ttccggtggg | cgcggggcat | gactatcgtc | gccgcactta | tgactgtctt | 1980 |
| ctttatcatg | caactcgtag | gacaggtgcc | ggcagcgctc | tgggtcattt | tcggcgagga | 2040 |
| ccgctttcgc | tggagcgcga | cgatgatcgg | cctgtcgctt | gcggtattcg | gaatcttgca | 2100 |

```
cgccctcgct caagccttcg tcactggtcc cgccaccaaa cgtttcggcg agaagcaggc    2160
cattatcgcc ggcatggcgg ccgacgcgct gggctacgtc ttgctggcgt tcgcgacgcg    2220
aggctggatg gccttcccca ttatgattct tctcgcttcc ggcggcatcg ggatgcccgc    2280
gttgcaggcc atgctgtcca ggcaggtaga tgacgaccat cagggacagc ttcaaggatc    2340
gctcgcggct cttaccagcc taacttcgat cattggaccg ctgatcgtca cggcgattta    2400
tgccgcctcg gcgagcacat ggaacgggtt ggcatggatt gtaggcgccg ccctatacct    2460
tgtctgcctc cccgcgttgc gtcgcggtgc atggagccgg gccacctcga cctgaatgga    2520
agccggcggc acctcgctaa cggattcacc actccaagaa ttggagccaa tcaattcttg    2580
cggagaactg tgaatgcgca accaaccct tggcagaaca tatccatcgc gtccgccatc     2640
tccagcagcc gcacgcggcg catctcgggc agcgttgggt cctggccacg ggtgcgcaac    2700
tagaattgat ctcctcgacc gccaattggg catctgagaa tcatctgcgt ttctcgcacg    2760
caacgtactt gcaacgttgc aactcctagt gttgtgaatc acaccccacc gggggtgggg   2820
attgcagtca ccgatttggt gggtgcgccc aggaagatca cgtttacata ggagcttgca    2880
atgagctact ccgtgggaca ggtggccggc ttcgccggag tgacggtgcg cacgctgcac    2940
cactacgacg acatcggcct gctcgtaccg agcgagcgca gccacgcggg ccaccggcgc    3000
tacagcgacg ccgacctcga ccggctgcag cagatcctgt tctaccggga gctgggcttc    3060
ccgctcgacg aggtcgccgc cctgctcgac gacccggccg cggacccgcg cgcgcacctg    3120
cgccgccagc acgagctgct gtccgcccgg atcgggaaac tgcagaagat ggcggcggcc    3180
gtggagcagg cgatggaggc acgcagcatg gaatcaacc tcaccccgga ggagaagttc     3240
gaggtcttcg gcgacttcga ccccgaccag tacgaggagg aggtccggga acgctggggg    3300
aacaccgacg cctaccgcca gtccaaggag aagaccgcct cgtacaccaa ggaggactgg    3360
cagcgcatcc aggacgaggc cgacgagctc acccggcgct tcgtcgccct gatggacgcg    3420
ggtgagcccg ccgactccga gggggcgatg gacgccgccg aggaccaccg gcagggcatc    3480
gcccgcaacc actacgactg cgggtacgag atgcacacct gcctgggcga gatgtacgtg    3540
tccgacgaac gtttcacgcg aaacatcgac gccgccaagc cgggcctcgc cgcctacatg    3600
cgcgacgcga tcctcgccaa cgccgtccgg cacaccccct gagcggtggt cgtggcccgg    3660
gtctcccgcc cggtctcacc ccacggctca ctcccgggcc acgaccaccg ccgtcccgta    3720
cgcgcacacc tcggtgccca cgtccgccgc ctccgtcacg tcgaaacgga agatccccgg    3780
gtaccgagct cgtcaggtgg cacttttcgg ggaaatgtgc gcggaacccc tatttgttta    3840
tttttctaaa tacattcaaa tatgtatccg ctcatgagac aataaccctg ataaatgctt    3900
caataatatt gaaaaggaa gagtatgagt attcaacatt tccgtgtcgc ccttattccc     3960
ttttttgcgg cattttgcct tcctgttttt gctcacccag aaacgctggt gaaagtaaaa    4020
gatgctgaag atcagttggg tgcacgagtg ggttacatcg aactggatct caacagcggt    4080
aagatccttg agagttttcg ccccgaagaa cgttttccaa tgatgagcac ttttaaagtt    4140
ctgctatgtg gcgcggtatt atcccgtatt gacgccgggc aagagcaact cggtcgccgc    4200
atacactatt ctcagaatga cttggttgag tactcaccag tcacagaaaa gcatcttacg    4260
gatggcatga cagtaagaga attatgcagt gctgccataa ccatgagtga taacactgcg    4320
gccaacttac ttctgacaac gatcggagga ccgaaggagc taaccgcttt tttgcacaac    4380 atggggatc atgtaactcg ccttgatcgt tgggaaccgg agctgaatga agccatacca    4440
aacgacgagc gtgacaccac gatgcctgta gcaatggcaa caacgttgcg caaactatta    4500
```

```
actggcgaac tacttactct agcttcccgg caacaattaa tagactggat ggaggcggat    4560
aaagttgcag gaccacttct gcgctcggcc cttccggctg gctggtttat tgctgataaa    4620
tctggagccg gtgagcgtgg gtctcgcggt atcattgcag cactgggcc  agatggtaag    4680 ccctcccgta tcgtagttat ctacacgacg gggagtcagg caactatgga tgaacgaaat    4740
agacagatcg ctgagatagg tgcctcactg attaagcatt ggtaactgtc agaccaagtt    4800
tactcatata tactttagat tgatttaaaa cttcattttt aatttaaaag gatctaggtg    4860
aagatccttt ttgataatct catgaccaaa atcccttaac gtgagttttc gttccactga    4920
gcgtcagacc ccgtagaaaa gatcaaagga tcttcttgag atcctttttt tctgcgcgta    4980
atctgctgct tgcaaacaaa aaaccaccg ctaccagcgg tggtttgttt gccggatcaa     5040
gagctaccaa ctcttttttcc gaaggtaact ggcttcagca gagcgcagat accaaatact    5100
gttcttctag tgtagccgta gttaggccac cacttcaaga actctgtagc accgcctaca    5160
tacctcgctc tgctaatcct gttaccagtg gctgctgcca gtggcgataa gtcgtgtctt    5220
accgggttgg actcaagacg atagttaccg gataaggcgc agcggtcggg ctgaacgggg    5280
ggttcgtgca cacagcccag cttggagcga acgacctaca ccgaactgag atacctacag    5340
cgtgagctat gagaaagcgc cacgcttccc gaagggagaa aggcggacag gtatccggta    5400
agcggcaggg tcggaacagg agagcgcacg agggagcttc caggggaaa cgcctggtat     5460 ctttatagtc ctgtcgggtt tcgccacctc tgacttgagc gtcgattttt gtgatgctcg    5520
tcaggggggc ggagcctatg gaaaaacgcc agcaacgcgg ccttttacg gttcctggcc     5580 ttttgctggc cttttgctca catgttcttt cctgcgttat cccctgattc tgtggataac    5640
cgtattaccg cctttgagtg agctgatacc gctcgccgca gccgaacgac cgagcgcagc    5700
gagtcagtga gcgaggaagc ggaagagcgc ccaatacgca aaccgcctct ccccgcgcgt    5760
tggccgattc attaatgcag ctggcacgac tagagtcccg ctgaggcggc gtagcaggtc    5820
agccgcccca gcggtggtca ccaaccgggg tggaacggcg ccggtatcgg gtgtgtccgt    5880
ggcgctcatt ccaacctccg tgtgtttgtg caggtttcgc gtgttgcagt ccctcgcacc    5940
ggcacccgca gcgaggggct cacgggtgcc ggtgggtcga ctagtttatt aatgatgatg    6000
atgatgatgc aggtgtttca ggatgaaatc cgaaagcaac ttgttgtatc cttcacgatc    6060
ctcccacatc gtgaggtgcg agcaatccct gaagacgtga agttccgaac cagctatttt    6120
ttcatgtatg actctggcca cgtttggcgt gacctcatcg tattcgccca ccgttataag    6180
ggtggggatc tttattgcag atattttgtc cgtgatatcc cagtccttta tcgtgccggt    6240
tatggtgaac tcattcgggc cgttcattat cctgtatacg tttcgccttt ccgcgtattc    6300
tagtgatttg agtacctcgg gcggccaatc tctgatctc  agcagatgct gatggtaaaa    6360
gtagttcacg gcctcctgat attctggatt tcgtaagat  ccagatgaac cgtatttttt    6420
aatggcatct ctgtactttg ccgggagctc gtcaatgagc ctgttcatct ccttcaccgt    6480
cagagggact gaagataagc ctccggatac gatgagccct tcagatgat  cctggtacttt    6540 gactgcgtat gccagcgcca gcgctccacc atatgatgac cccatcaaaa ataccttctc    6600
gttgccgaac agcttgatc  ttagggcctc tgcctcttcc acaccatagt caattgtgaa    6660
tttagactga tccggttcct cggatctacc gcatccaaac tgatcgtaga atagaaccgt    6720
tatcccttcc ttggtcatat ccctgagaga aagcaggtaa tcgtgggaca tgccggggcc    6780
cccgtgcatg gtcattagct ttgctttctc ctcagggggct ttgcacagct tgtaataaat    6840
```

```
ataaattccg tttacctttg cgtagttttc tatgcattcc tgatccatgg ccgctccctt   6900
ctctgacgcc gtccacgctg cctcctcacg tgacgtgagg tgcaagcccg gacgttccgc   6960
gtgccacgcc gtgagccgcc gcgtgccgtc ggctccctca gcccgggcgg ccgtgggagc   7020
ccgcctcgat atgtacaccc gagaagctcc cagcgtcctc ctgggccgcg atactcgacc   7080
accacgcacg cacaccgcac taacgattcg gccggcgctc gattcggccg gcgctcgatt   7140
cggccggcgc tcgattcggc cggcgctcga ttcggccggc gctcgattcg gccgagcaga   7200
agagtgaaca accaccgacc acgcttccgc tctgcgcgcc gtacccgacc tacctcccgc   7260
agctcgaagc agctcccggg agtaccgccg tactcacccg cctgtgctca ccatccaccg   7320
acgcaaagcc caacccgagc acacctcttg caccaaggtg ccgaccgtgg ctttccgctc   7380
gcagggttcc agaagaaatc gaacgatcca gcgcggcaag gttcaaaaag caggggttgg   7440
tggggaggag gttttggggg gtgtcgccgg gatacctgat atggctttgt tttgcgtagt   7500
cgaataattt tccatatagc ctcggcgcgt cggactcgaa tagttgatgt gggcgggcac   7560
agttgcccca tgaaatccgc aacgggggc gtgctgagcg atcggcaatg gcggatgcg    7620
gtgttgcttc cgcaccggcc gttcgcgacg aacaacctcc aacgaggtca gtaccggatg   7680
agccgcgacg acgcattggc aatgcggtac gtcgagcatt caccgcacgc gttgctcgga   7740
tctatcgtca tcgactgcga tcacgttgac gccgcgatgc gcgcattcga gcaaccatcc   7800
gaccatccgg cgccgaactg ggttgcacaa tcgccgtccg gccgcgcaca catcggatgg   7860
tggctcggcc ccaaccacgt gtgccgcacc gacagcgccc gactgacgcc actgcgctac   7920
gcccaccgca tcgaaaccgg cctcaagatc agcgtcggcg gcgatttcgc gtatggcggg   7980
caactgacca aaaacccgat tcaccccgat tgggagacga tctacggccc ggccaccccg   8040
tacacattgc ggcagctggc caccatccac acacccggc agatgccgcg tcggcccgat   8100
cgggccgtgg gcctgggccg caacgtcacc atgttcgacg ccacccggcg atgggcatac   8160
ccgcagtggt ggcaacaccg aaacggaacc ggccgcgact gggaccatct cgtcctgcag   8220
cactgccacg ccgtcaacac cgagttcacg acaccactgc cgttcaccga agtacgcgcc   8280
accgcgcaat ccatctccaa atggatctgg cgcaatttca ccgaagaaca gtaccgagcc   8340
cgacaagcgc atctcggtca aaaaggcggc aaggcaacga cactcgccaa acaagaagcc   8400
gtccgaaaca atgcaagaaa gtacgacgaa catacgatgc gagaggcgat tatctgatgg   8460
gcggagccaa aaatccggtg cgccgaaaga tgacggcagc agcagcagcc gaaaaattcg   8520
gtgcctccac tcgcacaatc caacgcttgt ttgctgagcc gcgtgacgat tacctcggcc   8580
gtgcgaaagc tcgccgtgac aaagctgtcg agctgcggaa gcaggggttg aagtaccggg   8640
aaatcgccga agcgatggaa ctctcgaccg ggatcgtcgg ccgattactg cacgacgccc   8700
gcaggcacgg cgagatttca gcggaggatc tgtcggcgta accaagtcag cgggttgtcg   8760
ggttccggcc ggcgctcggc actcggaccg gccggcggat ggtgttctgc ctctggcgca   8820
gcgtcagcta ccgccgaagg cctgtcatcg accggcttcg actgaagtat gagcaacgtc   8880
acagcctgtg attggatgat ccgctcacgc tcgaccgcta cctgttcagc tgccgcccgc   8940
tgggcatgag caacggccaa ctctcgttca a                                 8971
```

MICROORGANISM SENSITIVE TO LYSOZYME

TECHNICAL FIELD

The present invention relates to a microorganism of the genus *Rhodococcus* suitable for production of a recombinant protein, and more specifically, to a mutant strain more sensitive to lysozyme at a low concentration than a wild-type strain and capable of easily causing cell lysis. Use of the mutant strain makes it easier to extract and recover an expressed protein.

BACKGROUND ART

As a technique for expressing a recombinant protein in a microbial host, an expression system using *Escherichia coli* (*E. coli*) as a host has been generally and widely used. This is because *E. coli* is extremely easy to handle in a laboratory. More specifically, *E. coli* is confirmed as a safe microbial host and proliferates at a high rate, and its molecular biological operations in a laboratory are well established. On the other hand, development of host microorganisms having usefulness and advantages over *E. coli* in view of recombinant protein expression has progressed.

Microorganisms of the genus *Rhodococcus* are not pathogenic, except a few, and easily cultured in an ordinary laboratory. In addition to such essential conditions, they have the function as microbial catalysts, which is considered to be extremely useful from an industrial point of view. For these reasons, recently, various molecular biological techniques have been developed by use of such microorganisms. For example, in an attempt to add a further useful function to the microorganisms, techniques involving gene recombination has been developed. As a result, a shuttle vector was established which can replicate autonomously both in *E. coli* and in a microorganism of the genus *Rhodococcus* (R, De Mot et al., Microbiology 143, 3137-3147, (1997)). Furthermore, there is a report that a transposable transposon is present in a microorganism of the genus *Rhodococcus* (I, Nagy et al., J. Bacteriol. 179, 4635-4638 (1997)). Thus, it is expected to improve the microorganism in function, for example, by destroying the gene or integrating an exogenous gene into the chromosome.

In an attempt to further improve a microbial catalytic action based on such a molecular biological establishment, development of a vector for expressing a recombinant protein has been underway (JP Patent Publication (Kokai) No. 10-248578 A (1998)).

A microorganism of the genus *Rhodococcus*, namely, *Rhodococcus erythropolis* is not only useful as a microbial catalyst but also advantageous in that it can grow under a low temperature condition of 4° C. For this reason, it is expected that *Rhodococcus erythropolis* may produce a recombinant protein or the like in a temperature range where *E. coli* could not be used. Development of an inducible expression vector has been underway for such a purpose (the application already filed by Tamura, on Aug. 12, (2002)).

However, the cell wall of a microorganism of the genus *Rhodococcus* is particular and rigid in structure compared to those of other gram-positive bacteria. Therefore, extraction of a cellular content from the microorganism is complicated and difficult compared to the case of *E. coli*. More specifically, a microorganism of the genus *Rhodococcus* has an extremely strong resistance to a cell-wall lytic enzyme used generally for microbial cell lysis, such as lysozyme.

Examples of a cell lysis method include a method of exposing cell wall to a high-concentration antibiotic, such as penicillin, for a predetermined time to weaken the cell wall and then being subjected to cell lysis with lysozyme, and a method of applying ultrasonic treatment to bacterial cells for a long time to physically destroy them. However, these methods are complicated in process, it is difficult to treat a large amount of cells, and specimens are not likely to be treated uniformly. These problems are significant in view of industrial use. The effectiveness of an antibiotic such as penicillin is brought by inhibiting a de-novo synthesis of a cell wall and therefore the cell wall completed in synthesis is not affected by such an antibiotic. Therefore, the effect of such an antibiotic is considered to be low in low-temperature conditions where rapid growth is not expected.

It is known that the cell wall structure of a microorganism of the genus *Rhodococcus* is commonly seen in bacteria of the genus *Corynebacterium* (C. E. Barry III et al., Prog. Lipid Res. 37, 143-179 (1988)) and an invention similar to the present invention has been made in view of an object of facilitating a molecular biological operation such as transformation (JP Patent Publication (Kokoku) No. 01-003475 B (1989), T. Hirasawa et al., J. Bacteriol. 182, 2696-2701 (2000)).

DISCLOSURE OF THE INVENTION

The present invention is directed to providing a microorganism of the genus *Rhodococcus* improved in sensitivity to lysozyme and capable of being lysed with lysozyme at a low concentration, the microorganism allowing recovery of the protein by treatment of the microorganism with lysozyme after an exogenous gene is integrated to the microorganism and allowed to express. Furthermore, the present invention provides a method of producing an exogenous protein by use of the microorganism of the genus *Rhodococcus* having a high sensitivity to lysozyme.

The present inventors conducted studies with a view toward to attain an expression system for a recombinant protein by use of a microorganism of the genus *Rhodococcus* by overcoming a difficulty in extracting a cellular content. As a result, they found a novel microorganism of the genus *Rhodococcus* more sensitive to lysozyme at an extremely low concentration than a wild type strain. More specifically, mutation was induced in a wild type strain to obtain a mutant that cannot grow in a medium containing lysozyme. Mutation is usually induced by a chemical mutagen such as nitrosoguanidine or irradiation with radioactive rays. However, taking safety and convenience into consideration, ultraviolet ray irradiation is employed in the present invention. Furthermore, the present inventors found that cell lysis can be performed only by lysozyme treatment without pretreatment with penicillin or the like, and that a cellular content such as a recombinant protein accumulated in the cells can be extracted in a much easier manner than a conventional method. Based on these findings, the present invention was completed.

More specifically, the present invention includes (1) A mutant of a microorganism of the genus *Rhodococcus* having a higher sensitivity to lysozyme than a wild-type microorganism of the genus *Rhodococcus*.

(2) The microorganism of the genus *Rhodococcus* according to item (1), in which the microorganism of the genus *Rhodococcus* is *Rhodococcus erythropolis*.

(3) The microorganism of the genus *Rhodococcus* according to item (2), in which the *Rhodococcus erythropolis* is *Rhodococcus erythropolis* strain L-65 (deposited on Jun. 12, 2002, originally at the International Patent Organism Depositary of the National Institute of Advanced Industrial Science and Technology (Tsukuba Central 6, 1-1-1 Higashi, Tsukuba, Ibaraki, Japan) under Accession No. FERM BP-8443) or *Rhodococcus erythropolis* strain L-88 (deposited on Jun. 12, 2002, originally at the International Patent Organism Depositary of the National Institute of Advanced Industrial Science and Technology (Tsukuba Central 6, 1-1-1 Higashi, Tsukuba, Ibaraki, Japan, Accession No. FERM BP-8444).

(4) A method of producing a protein comprising transforming a mutant of a microorganism of the genus *Rhodococcus* having a higher sensitivity to lysozyme than a wild-type microorganism of the genus *Rhodococcus* by a gene encoding an exogenous protein; expressing the gene; and treating the microorganism of the genus *Rhodococcus* with lysozyme, thereby extracting and recovering the protein.

(5) The method of producing a protein according to item (4), in which the microorganism of the genus *Rhodococcus* is *Rhodococcus erythropolis*.

(6) The method of producing a protein according to item (5), in which the *Rhodococcus erythropolis* is *Rhodococcus erythropolis* strain L-65 (Accession No. FERM BP-8443) or *Rhodococcus erythropolis* strain L-88 (Accession No. FERM BP-8444).

Now, the present invention will be explained in detail.

A microorganism of the genus *Rhodococcus* according to the present invention is a mutant microorganism of the genus *Rhodococcus*, which has a higher sensitivity to lysozyme than a wild-type microorganism of the genus *Rhodococcus*. The microorganism of the genus *Rhodococcus* is not limited to a specific species and includes *Rhodococcus erythropolis*, *Rhodococcus fascians*, and *Rhodococcus opacus*. The wild-type microorganism of the genus *Rhodococcus* refers to a microorganism belonging to the genus *Rhodococcus* and having no genetic mutation, for example, *Rhodococcus erythropolis* strain JCM 3201. More specifically, the microorganism of the genus *Rhodococcus* according to the present invention having a higher sensitivity to lysozyme is a mutant derived from a wild-type microorganism of the genus *Rhodococcus* as a parent strain, and having an increased sensitivity to lysozyme compared to the parent strain. The phrase "having an increased sensitivity to lysozyme" means that cell lysis may occur at a low lysozyme concentration. If cell growth is inhibited when lysozyme is added to a medium where a microorganism is cultured, it is said that the microorganism has a sensitivity to lysozyme. The sensitivity to lysozyme can be expressed by a minimum lysozyme concentration capable of inhibiting the growth of a microorganism (a minimum growth inhibitory lysozyme concentration). A source providing lysozyme is not limited, for example, egg-white lysozyme may be used. The minimum growth inhibitory lysozyme concentration is obtained as follows: for example, a microorganism of the genus *Rhodococcus* is prepared in a liquid medium at a density of $1 \times 10$ to $1 \times 10^5$ cells/10 µl. Lysozyme is serially diluted from a concentration of several hundreds µg/ml to several µg/ml. Each of the serial dilutions is added to 10 µl of the liquid medium prepared above. The microorganism is cultured for several days. The lysozyme concentration that inhibits the growth of a microorganism of the genus *Rhodococcus* represents the minimum growth inhibitory lysozyme concentration. Alternatively, the degree of sensitivity to lysozyme can be determined by adding lysozyme to a predetermined concentration of a microorganism of the genus *Rhodococcus*, and monitoring a change in absorbence while culturing. In this case, a strain non-sensitive to lysozyme continues to grow without causing cell lysis by lysozyme, and thus absorbence increases with time, whereas a strain sensitive to lysozyme causes cell lysis by lysozyme, and absorbence decreases rapidly.

The minimum growth inhibitory lysozyme concentration of a microorganism of the genus *Rhodococcus* having a high sensitivity to lysozyme according to the present invention is preferably 50 µg/ml or less, more preferably, 25 µg/ml or less, and most preferably 13 µg/ml or less. This is equal to or less than ⅛, preferably ¹⁄₁₆, and particularly preferably, ¹⁄₃₀ of the minimum growth inhibitory lysozyme concentration of a wild type, that is, a parent strain.

A microorganism of the genus *Rhodococcus* generally has a high resistance to lysozyme, so that the microorganism cannot be lysed with lysozyme alone. Therefore, an antibiotic such as penicillin must be used at a high concentration to inhibit the cell wall synthesis of the microorganism during growth to weaken the cell wall, and then lysozyme is applied to the microorganism. However, the organism of the genus *Rhodococcus* according to the present invention can be lysed with lysozyme alone.

The organism of the genus *Rhodococcus* having a high sensitivity to lysozyme according to the present invention can be obtained by treating a wild-type microorganism of the genus *Rhodococcus* such as *Rhodococcus erythropolis* strain JCM 3201 with a chemical mutagen or a physical mutagen, culturing it in an agar medium, transferring the colonies thus grown onto a medium containing lysozyme and a medium not containing lysozyme, culturing both, and selecting a bacterial cell not grown in the medium containing lysozyme. The sensitivity to lysozyme can be determined by the aforementioned sensitivity test. Examples of such chemical mutagens include alkylation agents such as N-methyl-N'-nitro-N-nitrosoguanidine and mustard gas, non-alkylation agents such as hydradine and nitrite, DNA nucleotide analogs such as 5-bromo uracil, 2-aminopterin, and DNA intercalators, such as acrydine orange. Examples of such physical mutagens include ultraviolet rays, X-rays, γ-rays, and neutron beam. A method of treating a microorganism with a mutagen, the concentration of a chemical mutagen to be used, and the intensity of a physical mutagen to be used may be appropriately selected in accordance with a known method.

Examples of such an microorganism of the genus *Rhodococcus* having a high sensitivity to lysozyme according to the present invention include *Rhodococcus erythropolis* strain L-65 (Accession No. FERM BP-8443) and *Rhodococcus erythropolis* strain L-88 (Accession No. FERM BP-8444).

In a microorganism of the genus *Rhodococcus* having a high sensitivity to lysozyme according to the present invention, its sensitivity to lysozyme is higher than that of a wild-type strain, that is, a parent stain; however, the sensitivity to at least one member of antibiotics such as ampicillin, kanamycin, chloramphenicol, tetracycline, and thiostreptone is equal to that of the wild strain and thus has no significant difference. Even if the sensitivity differs between them, the difference from the wild type is not so large as that from lysozyme sensitivity. More specifically, a microorganism of the genus *Rhodococcus* having a high sensitivity to the lysozyme according to the present invention has a resistant gene to a certain antibiotic integrated as a selection marker. Therefore, when the microorganism of the present invention is transformed by an expression vector having an exogenous gene integrated therein and a transformant is selected based on the selection marker, non-transformed microorganism of the genus *Rhodococcus* cannot grow since the sensitivity to the antibiotic is not lowered and thus only transformant can be selected. In this respect, as long as a microorganism of the genus *Rhodococcus* having a high sensitivity to lysozyme according to the present invention has a sensitivity to the antibiotic to be used for selection even if the sensitivity to other antibiotics is low, it can be used.

A recombinant protein can be efficiently obtained by using a microorganism of the genus *Rhodococcus* having a high sensitivity to lysozyme according to the present invention. To explain more specifically, the protein can be obtained by transforming a microorganism of the genus *Rhodococcus* having a high sensitivity to lysozyme according to the present invention with a gene encoding an exogenous protein derived from other species, culturing the transformed *Rhodococcus* microorganism in the conditions where the gene can be expressed, thereby expressing the exogenous protein, treating the microorganism having the expressed protein therein with lysozyme, thereby extracting the protein, and purifying and recovering the protein from the extract solution. The transformation of a microorganism of the genus *Rhodococcus* of the present invention may be performed in accordance with a known method. At this time, a transformation efficiency of a microorganism of the genus *Rhodococcus* with a reduced sensitivity to lysozyme is equivalent to that of a wild type strain, that is, a parent strain, even if there is a difference between them, the difference is not so significant. In some cases, the transformation efficiency is more or less lowered by the effect of introduction of mutation; however, there is no case where the efficiency of expressing and producing an exogenous protein is significantly reduced.

Transformation can be performed by using a known expression vector for a microorganism of the genus *Rhodococcus* or by expression vector pHN170 constructed by the present inventors such that the expression of the vector can be induced by thiostreptone.

A microorganism of the genus *Rhodococcus* transformed by integrating an exogenous gene therein is cultured. After the exogenous gene is expressed, the cells of the microorganism are collected by centrifugation, or the like, suspended in a buffer solution, such as a phosphate buffer, having lysozyme dissolved therein, and incubated at a temperature near an optimal temperature of lysozyme for several tens to several hours. The cells of the microorganism are lysed by the action of lysozyme and the expressed protein is extracted into the buffer solution. The extracted protein is purified by a known protein purification method to obtain the protein. The concentration of lysozyme to be used in cell lysis is 0.1 mg/ml to 10 mg/ml, preferably about 1 mg/ml. Purification can be performed by use of any separation and purification method. For example, ammonium sulfate precipitation, gel filtration, ion exchange chromatography, and affinity chromatography may be used singly or in an appropriate combination. In the case where an expression product is present in the form of a fusion protein with GST, His tag, it may be purified by use of the nature of a peptide or a protein that is fused to a desired protein. To explain more specifically, since GST has an affinity for glutathione, the desired protein can be efficiently purified by affinity chromatography by use of a column having a carrier to which glutathione is attached.

The specification includes the specification and/or contents of the drawings of JP Patent Application No. 2002-239554 based on which the present application claims the priority.

BRIEF DESCRIPTION OF THE DRAWINGS

The application contains at least one drawing executed in color. Copies of this patent or patent application publication with color drawing(s) will be provided by the Office upon request and payment of the necessary fee.

BEST MODE FOR CARRYING OUT THE INVENTION

The present invention will be now explained with reference to Examples, which should not be construed as limiting the present invention.

EXAMPLE 1

Production of Lysozyme-sensitive Bacterial Strain

Figure 1:
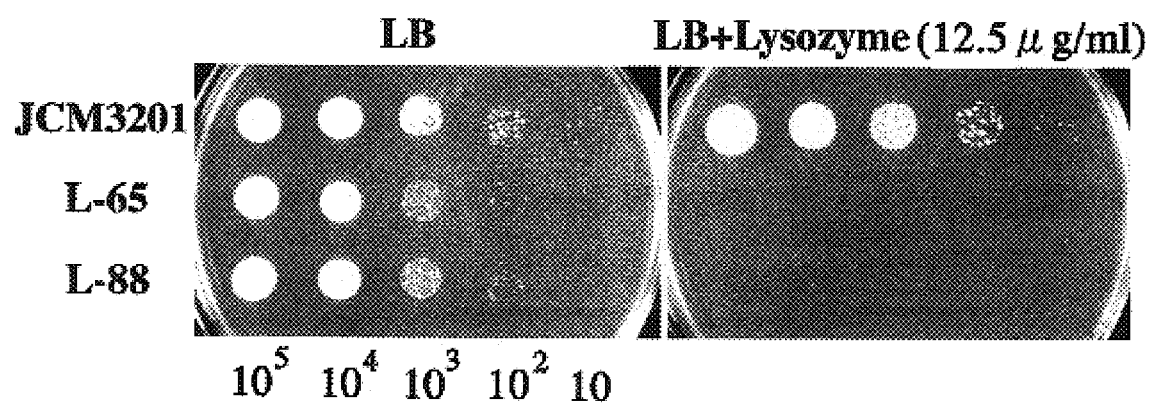
FIG. 1 shows photographs of LB agar mediums onto which serially diluted culture solutions are spotted for comparing their growth.

*Rhodococcus erythropolis* strain JCM 3201 was cultured in LB medium (1% Difco Bacto Tryptone, 0.5% Difco Yeast Extract, and 1% sodium chloride) with shaking at 30° C. The LB medium was taken in the middle of the logarithmic growth period and appropriately diluted. The dilution was applied onto an LB medium plate containing 1.5% agar at a density of about $5 \times 10^3$ bacterial cells per plate, and the application surface was irradiated with 254 nm ultraviolet ray by means of an ultraviolet-ray irradiation apparatus (manufactured by Atto, power: 4 W) placed at a distance of 15 cm from the application surface for 20 seconds. The medium irradiated with the ultraviolet ray was cultured stand still at 30° C. for 2 days to obtain about $5 \times 10^2$ colonies per plate. The colonies were scraped by a cocktail stick and inoculated onto a 96-well plate filled with about 150 µl of LB medium. After the colonies were sufficiently suspended, a part of the suspension was inoculated onto a 96-well plate filled with 150 µl of LB medium containing lysozyme derived from egg-white in a concentration of 50 µg/ml (manufactured by Sigma, hereinafter simply referred to as "lysozyme"). The couple of plates thus obtained were cultured stand still at 30° C. for 2 days. As a result, a mutant strain capable of growing only in lysozyme-free LB medium was obtained as a lysozyme sensitive strain. Examples of such a novel lysozyme sensitive microorganism according to the present invention include *Rhodococcus erythropolis* strain L-65 and *Rhodococcus erythropolis* strain L-88, which was originally deposited on Jun. 12, 2002 under Accession Nos. FERM BP-8443 and FERM BP-8444, respectively at the International Patent Organism Depositary of the National Institute of Advanced Industrial Science and Technology (Tsukuba Central 6, 1-1-1 Higashi, Tsukuba, Ibaraki, Japan). A request for transferring the microorganisms from the original deposition to the international deposition based on the Budapest Treaty was made and accepted as of Jul. 28, 2003. The bacterial strain was inoculated in LB medium and cultured with shaking at 30° C. A part of the culture solution was taken in the middle of the logarithmic growth period and diluted with fresh LB medium so as to contain $1\times10^5$, $1\times10^4$, $1\times10^3$, $1\times10^2$, and $1\times10$ cells in 10 µl of the LB medium. The diluted culture solutions thus prepared were spotted onto each of LB agar mediums containing lysozyme in concentrations of 50, 25, 12.5 and 6.3 µg/ml. After the mediums were cultured at 30° C. for 2 days, the presence or absence of bacterial cells grown on mediums was checked. In this manner, the minimum growth inhibition concentration was determined (Table 1 and FIG. 1). As shown in the figure, the culture solutions of bacterial strains JCM3201, L-65, and L-88 were dropped onto an LB agar medium containing no lysozyme and an LB agar medium containing lysozyme (12.5 µg/ml) and then subjected to culturing. The bacterial strains JCM3201, L-65, and L-88 cells were dropped respectively onto the upper stage, the middle stage, and the lower stage of the LB agar medium and cultured as shown in FIG. 1. The numbers of bacterial cells contained in culture solutions were $1\times10^5$, $1\times10^4$, $1\times10^3$, $1\times10^2$, and $1\times10$ cells in this order from the left.

TABLE 1

| Bacterial strain | Deposition No. | Minimum growth-inhibiting lysozyme concentration (µg/ml) |
|---|---|---|
| *Rhodococcus erythropolis* strain L-65 | FERM BP-8443 | 12.5 |
| *Rhodococcus erythropolis* strain L-88 | FERM BP-8444 | 12.5 |
| *Rhodococcus erythropolis* strain JCM 3201 | ATCC25544 | >400 |

EXAMPLE 2

Figure 2:
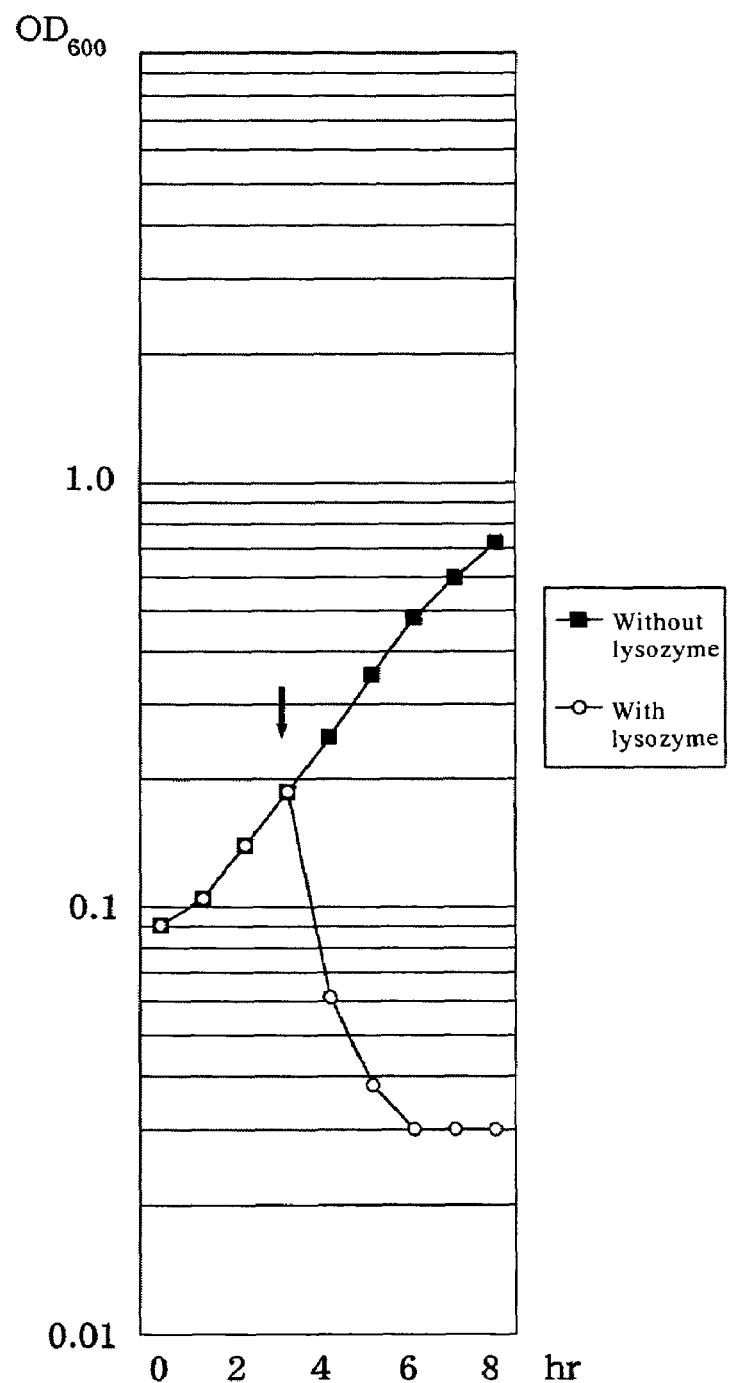
FIG. 2 is a graph showing a growth curve of *Rhodococcus erythropolis* strain L-65.

Turbidity Change of *Rhodococcus erythropolis* Strain L-65 Culture Solution by Addition of Lysozyme To 100 ml of LB medium, *Rhodococcus erythropolis* strain L-65 was inoculated and cultured with shaking at 30° C. The absorbence ($OD_{600}$) of the culture solution was measured at an absorption wavelength of 600 nm every hour from the beginning of the logarithmic growth period. When $OD_{600}$ reached about 0.2, the volume of the culture solution was divided into halves. To one of them, lysozyme was added to a final concentration of 12.5 µg/ml. No lysozyme was added to the other. While both solutions were further cultured continuously, the absorbence was measured. The results are shown in FIG. 2. The growth profiles of *Rhodococcus erythropolis* strain L-65 culture solutions with Lysozyme (12.5 µg/ml) and without lysozyme were shown by absorbence at 600 nm. When $OD_{600}$ reached about 0.2, lysozyme was added (Indicated by the arrow in the figure). When lysozyme was added, a sharp decrease in absorbence was observed. This is considered because bacterial cell lysis was caused by lysozyme.

EXAMPLE 3

Figure 3:
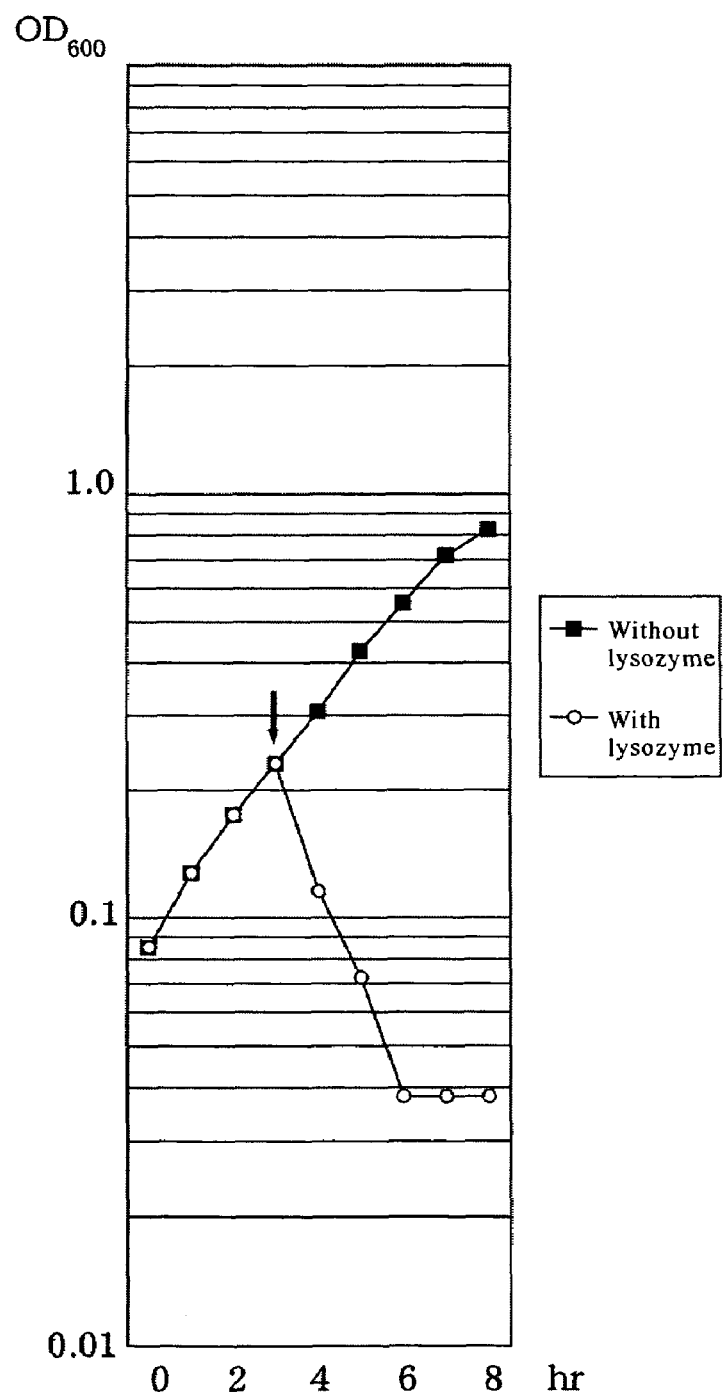
FIG. 3 is a graph showing a growth curve of *Rhodococcus erythropolis* strain L-88.

Turbidity Change of *Rhodococcus erythropolis* Strain L-88 Culture Solution by Addition of lysozyme The same operation as in Example 2 was performed by use of *Rhodococcus erythropolis* strain L-88. Absorbence was measured and the results are shown in FIG. 3. The growth profiles of culture solutions of *Rhodococcus erythropolis* strain L-88 with lysozyme (12.5 µg/ml) and without lysozyme were shown by absorbence at 600 nm. When $OD_{600}$ reached about 0.2, lysozyme was added (Indicated by the arrow in the figure). When lysozyme was added, a sharp decrease in absorbence was observed. This is considered because bacterial cell lysis was caused by lysozyme.

COMPARATIVE EXAMPLE 1

Figure 4:
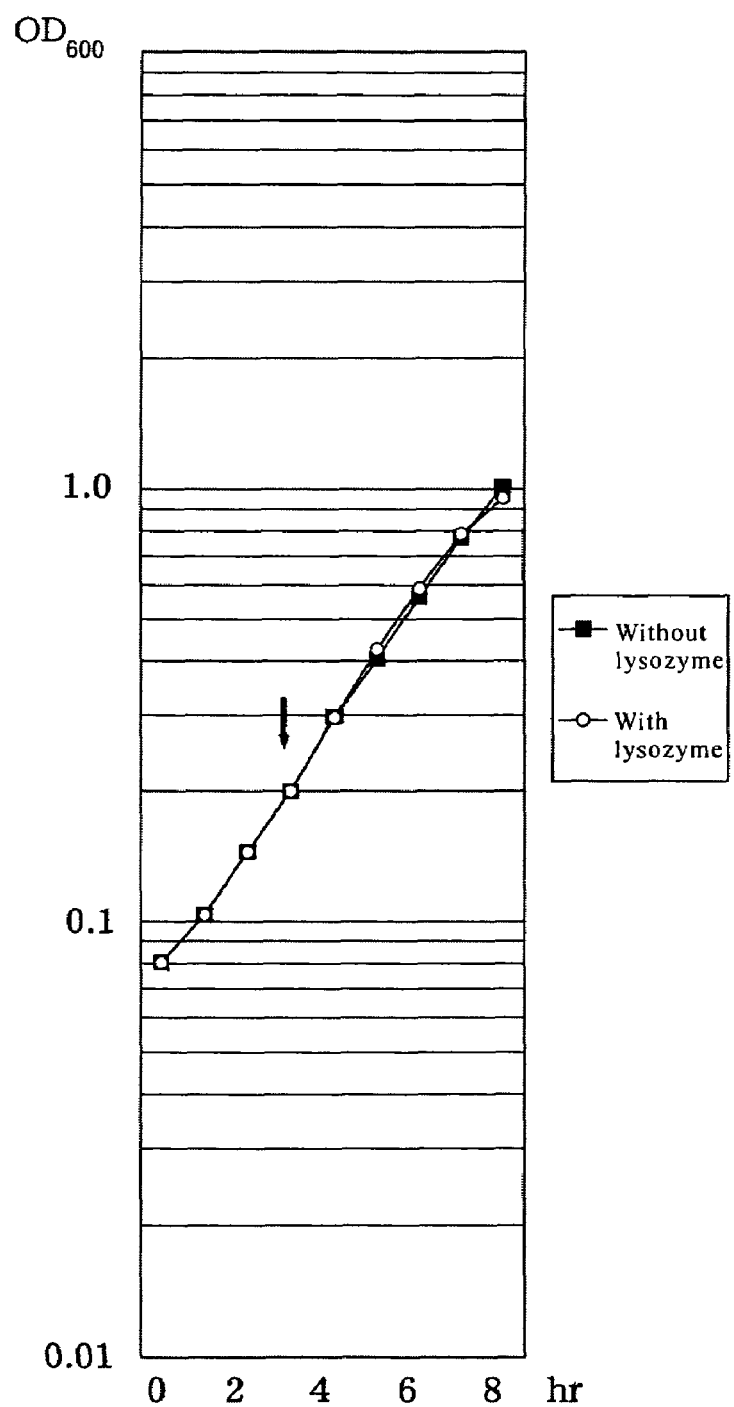
FIG. 4 is a graph showing a growth curve of *Rhodococcus erythropolis* strain JCM 3201.

Turbidity Change of *Rhodococcus erythropolis* Strain JCM 3201 Culture Solution by Addition of Lysozyme The same operation as in Example 2 was performed by use of *Rhodococcus erythropolis* strain JCM 3201. Absorbence was measured and the results are shown in FIG. 4. The growth profiles of culture solutions of *Rhodococcus erythropolis* strain JCM 3201 with lysozyme (12.5 µg/ml) and without lysozyme were shown by absorbence at 600 nm. When $OD_{600}$ reached about 0.2, lysozyme was added (Indicated by the arrow in the figure). Regardless of the presence or absence of lysozyme, the same tendency of growth was observed.

EXAMPLE 4

Sensitivity of Lysozyme Sensitive Bacterial Strain to Ampicillin

The sensitivity of *Rhodococcus erythropolis* strain L-65 and L-88 to ampicillin was determined in the same manner as in Example 1. To explain more specifically, the bacterial cells of each strain were inoculated in LB medium and cultured with shaking at 30° C. A part of the culture solution was taken in the middle of logarithmic growth period and diluted with fresh LB medium so as to contain $1\times10^5$, $1\times10^4$, $1\times10^3$, $1\times10^2$, and $1\times10$ cells in 10 µl of the LB medium. The diluted culture solutions thus prepared were dropped onto each of LB agar mediums containing lysozyme in concentrations of 15, 10, 1, and 0.1 µg/ml. After the mediums were cultured at 30° C. for 2 days and the presence or absence of bacterial cells grown on the mediums was checked. In this manner, the minimum growth inhibition concentration was determined (Table 2). Similarly, the wild type and the mutant strain were compared for sensitivity to kanamycin, chloramphenicol, tetracycline, and thiostreptone; however, no significant difference was observed between them.

TABLE 2

| Bacterial strain | Deposition No. | Minimum growth-inhibiting ampicillin concentration (µg/ml) |
|---|---|---|
| *Rhodococcus erythropolis* strain L-65 | FERM BP-8443 | 1 |
| *Rhodococcus erythropolis* strain L-88 | FERM BP-8444 | 1 |
| *Rhodococcus erythropolis* strain JCM 3201 | ATCC25544 | 15 |

EXAMPLE 5

Transformation Efficiency of Lysozyme Sensitive Strain

The transformation of *Rhodococcus erythropolis* was performed by an electroporation method. The method will be described in detail below. *Rhodococcus erythropolis* strain JCM 3201, L-65, and L-88 were cultured in 100 ml of LB medium with shaking at 30° C. until they reach their logarithmic growth periods. The culture solutions were cooled on ice for 30 minutes, and centrifugally separated to recover cells. To the recovered cells, 100 ml of ice-cooled sterilized water was added, stirred well, and again centrifugally separated to recover cells. To the recovered cells, 100 ml of an ice-cooled 10% glycerin solution was added, stirred well, and centrifugally separated to recover cells. The cells were washed again with the ice-cooled 10% glycerin solution and suspended in 5 ml of an ice-cold 10% glycerin solution. Then, 400 µl of the resultant cells were mixed with plasmid DNA (pHN144; Nakashima and Tamura; the full length sequence is represented by SEQ ID No: 1) capable of self-replicating in *Rhodococcus erythropolis*. The mixture solution was transferred to an electroporation cuvette (0.2 cm gap cuvette manufactured by Bio-Rad) and applied with an electric pulse by a gene introduction apparatus, gene pulser II, (manufactured by Bio-Rad) at an electric field of 12.5 kV/cm in strength, a capacitance of 25 µF (the pulse controller), and an external resistance of 400 Ω. The mixture of cells and DNA treated with the electric pulse was mixed with 1 ml of LB medium and cultured at 30° C. for 4 hours. Thereafter, cells were collected and applied onto LB agar medium containing thiostreptone in a concentration of 10 µg/ml and cultured at 30° C. for 3 days to obtain transformants for each case. The transformation efficiency (the number of colonies formed) per 1 µg of DNA is shown in Table 3.

TABLE 3

| Bacterial strain | Deposition No. | Transformation efficiency rate |
| --- | --- | --- |
| *Rhodococcus erythropolis* strain L-65 | FERM BP-8443 | $2.6 \times 10^5$ |
| *Rhodococcus erythropolis* strain L-88 | FERM BP-8444 | $2.5 \times 10^5$ |
| *Rhodococcus erythropolis* strain JCM 3201 | ATCC25544 | $4.0 \times 10^5$ |

EXAMPLE 6

Extraction of Recombinant Protein Produced by *Rhodococcus erythropolis* Strain L-65

Figure 5:
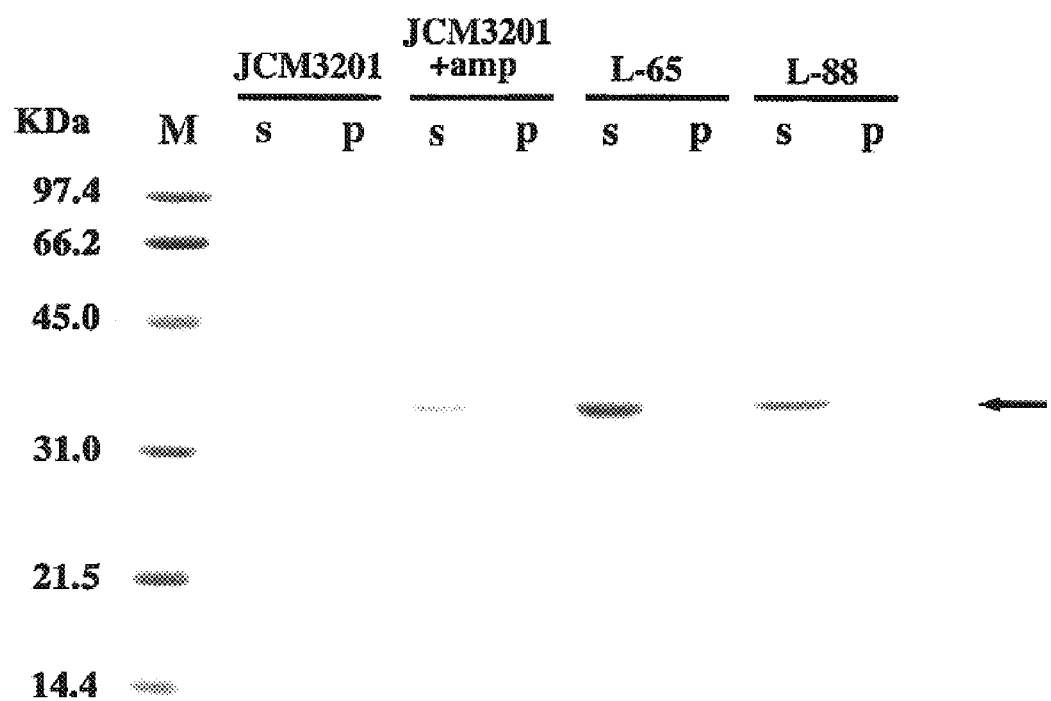
FIG. 5 shows SDS polyacrylamide electrophoresis of the cases where a PIP protein was expressed by *Rhodococcus erythropolis* strain L-65, L-88 and JCM3201.

A plasmid (pHN170, Nakashima and Tamura: the full length sequence is represented by SEQ ID No: 2) was constructed such that it could self-replicate in a bacterial cell of *Rhodococcus erythropolis* and could be induced by thiostreptone to express a proline iminopeptidase (hereinafter referred to as "PIP") protein (T. Tamura et al., FEBS Lett. 398, 101-105 (1996)) having a 6× histidine tag at the C terminal. This plasmid was introduced into *Rhodococcus erythropolis* strain L-65 by an electroporation method. Transformants were screened on LB agar medium containing tetracycline (20 µg/ml). The transformants were inoculated on 4 ml of LB medium containing tetracycline (8 µg/ml) and cultured with shaking at 30° C. until the absorbence at an absorption wavelength of 600 nm reached 0.8. The entire culture solution was added to 40 ml of LB medium containing thiostreptone (1 µg/ml) and cultured with rotation in a vaned flask for 16 hours. After PIP protein was induced to express, bacterial cells were centrifugally collected at 1,500×g for 15 minutes. After the cells thus collected was suspended in 4 ml of a 50 mM phosphate buffer (pH8.0) containing 300 mM salt, lysozyme was added so as to obtain a final concentration of 1 mg/ml. The resultant solution was incubated at 37° C. for one hour, cooled on ice, and centrifuged at 10,000×g for 15 minutes to separate the supernatant (s) and the precipitate (p). An aliquot of 1 ml was taken from the obtained supernatant (s) and placed in another microcentrifuge tube. To the microcentrifuge tube, 50 µl of Ni-NTA Superflow (manufactured by QIAGEN) was added, which had been previously equilibrated with a 50 mM phosphate buffer (pH 8.0) containing 300 mM salt. The resultant mixture was incubated at 4° C. for one hour while turning it upside down, washed three times with 1 ml of a 50 mM phosphate buffer (pH 6.0) containing 300 mM salt and 10% glycerin, and thereafter, eluted with 50 µl of a 50 mM phosphate buffer (pH 6.0) containing 500 mM EDTA, 300 mM salt and 10% glycerin to obtain 6× histidine-fused PIP protein. An aliquot (10 µl) was taken from the protein thus obtained and subjected to SDS polyacrylamide gel electrophoresis. As a result, a clear band was detected near the molecular weight (34.3 KDa), which was predicted from the amino acid sequence of the 6× histidine-fused PIP protein (FIG. 5). On the other hand, the precipitate (p) was resuspended in 1 ml of a 100 mM sodium dihydrogen phosphate −10 mM tris chloride buffer (pH 8.0) containing 8M urea, allowed to stand alone for 30 minutes, and subjected to centrifugation at 10,000×g for 15 minutes. The resultant supernatant was transferred to a new microcentrifuge tube, 50 µl of Ni-NTA Superflow, which had been previously equilibrated with a 100 mM sodium dihydrogen phosphate −10 mM tris chloride buffer (pH 8.0) containing 8M urea, was added to the microcentrifuge tube, and incubated at room temperature for one hour while turning upside down. After the microcentrifuge tube was washed three times with 1 ml of a 100 mM sodium dihydrogen phosphate −10 mM tris chloride buffer (pH 6.3) containing 8M urea, it was subjected to elution with 50 µl of a 100 mM sodium dihydrogen phosphate −10 mM tris chloride buffer (pH 8.0) containing 500 mM EDTA and 8M urea to obtain 6× histidine-fused PIP protein. An aliquot (10 µl) was taken from the protein thus obtained and subjected to SDS polyacrylamide gel electrophoresis (FIG. 5). Reference symbol M represents a molecular marker and molecular weight is shown at the left side of the figure to indicate an approximate molecular weight of each band. Band patterns of individual lanes are shown in FIG. 5 as follows.

Lane 1 (JCM 3201,s) shows an electrophoretic pattern of a sample obtained from the supernatant in the case where PIP is expressed by bacterial strain JCM 3201. Since cell lysis rarely takes place in a buffer solution under nondenaturation condition (containing no urea), a desired band (indicated by the arrow) is not detected. Lane 2 (JSM3201, p) shows an electrophoretic pattern of a sample obtained from the precipitate in the case where PIP is expressed by bacterial strain JSM 3201. Lysis takes place slightly in a buffer solution under denaturation conditions (containing urea) and thus a thin band of interest is detected.

Lane 3 (JCM3201+amp,s) shows an electrophoretic pattern of a sample obtained from the supernatant in the case where PIP is expressed by bacterial strain JCM 3201 where the sample is treated with ampicillin for 2 hours before cell collection. Since the sensitivity to lysozyme is increased by the treatment with ampicillin, cell lysis takes place even in nondenaturation conditions. As a result, a desired band can be clearly confirmed.

Lane 4 (JSM3201+amp, p) shows an electrophoretic pattern of a sample obtained from the precipitate in the case where PIP is expressed by bacterial strain JCM 3201 where the sample is treated with ampicillin for 2 hours before cell collection. It is considered that even though the cells previously treated with ampicillin do not cause cell lysis in a buffer under the nondenaturation conditions, they lyse in a buffer under denaturation conditions to give a detectable desired band.

Lane 5 (L-65, s) shows an electrophoretic pattern of a sample obtained from the supernatant in the case where PIP is expressed by bacterial strain L-65. Cells were lysed completely with lysozyme treatment to give a detectable desired band.

Lane 6 (L-65, p) shows an electrophoretic pattern of a sample obtained from the precipitate in the case where PIP is expressed by bacterial strain L-65. Since the precipitate is considered to contains only residual cells after lysis, the desired band is not detected.

Lane 7 (L-88, s) shows the electrophoretic pattern of a sample obtained from the supernatant in the case where PIP is expressed by bacterial strain L-88. The same phenomenon as in the case of bacterial stain L-65 is considered.

Lane 8 (L-88, p) shows the electrophoretic pattern of a sample obtained from the precipitate in the case where PIP is expressed by bacterial strain L-88. The same phenomenon as in the case of stain L-65 is considered.

As for the antibiotic used in the aforementioned operation, a required amount of a solution containing 5 mg of tetracycline dissolved in 1 ml of 50 wt % ethanol or 10 mg of thiostreptone dissolved in 1 ml of dimethylsulfoxide was used.

EXAMPLE 7

Extraction of Recombinant Protein Produced by *Rhodococcus erythropolis* Strain L-88

The same operation as in Example 6 was performed except that *Rhodococcus erythropolis* strain L-88 was used in place of *Rhodococcus erythropolis* strain L-65 (FIG. 5).

COMPARATIVE EXAMPLE 2

Extraction of Recombinant Protein Produced by *Rhodococcus erythropolis* Strain JCM 3201

The same operation as in Example 6 was performed except that *Rhodococcus erythropolis* strain JCM 3201 was used in place of *Rhodococcus erythropolis* strain L-65 (FIG. 5).

COMPARATIVE EXAMPLE 3

Extraction of Recombinant Protein Produced by *Rhodococcus erythropolis* Strain JCM 3201

A transformant was prepared in the same manner as in Example 6 except that *Rhodococcus erythropolis* strain JCM 3201 was used in place of *Rhodococcus erythropolis* strain L-65. The expression of PIP protein was induced by thiostreptone. Two hours before cell collection, 480 µl of an aqueous solution of ampicillin (50 mg/ml) was added (a final concentration of 600 µg/ml) and subjected to cell collection. Thereafter, the same operations as in Example 6 were performed and the obtained sample was subjected to electrophoresis (FIG. 5).

All publications, patents and patent applications cited herein are incorporated herein in its entirety by reference.

INDUSTRIAL APPLICABILITY

As shown in Examples, a microorganism of the genus *Rhodococcus* of the present invention has an increased sensitivity to lysozyme compared to a wild type strain. The transformation efficiency of the microorganism of the present invention is not significantly changed from that of the wild-type stain. It is therefore possible to efficiently transform a microorganism of the genus *Rhodococcus* of the present invention by a gene encoding the exogenous protein, express the exogenous protein, cause cell lysis with lysozyme, and extract and recover the protein easily.

Sequence listing free text
  SEQ ID No. 1: Plasmid pHN 144
  SEQ ID No. 2: Plasmid pHN 170

The invention claimed is:

1. An isolated microorganism of the genus *Rhodococcus* that is *Rhodococcus erythropolis* strain L-65 (Accession No. FERM BP-8443) or *Rhodococcus erythropolis* strain L-88 (Accession No. FERM BP-8444).

* * * * *